United States Patent
Para et al.

(10) Patent No.: US 7,074,814 B2
(45) Date of Patent: Jul. 11, 2006

(54) 3-SUBSTITUTED INDOLES AND DERIVATIVES THEREOF AS THERAPEUTIC AGENTS

(75) Inventors: Kimberly Suzanne Para, Ann Arbor, MI (US); Charles John Stankovic, Saline, MI (US); Melean Visnick, Ann Arbor, MI (US)

(73) Assignee: Warner-Lambert Company LLC, Morris Plains, NJ (US)

( * ) Notice: Subject to any disclaimer, the term of this patent is extended or adjusted under 35 U.S.C. 154(b) by 27 days.

(21) Appl. No.: 10/860,336

(22) Filed: Jun. 3, 2004

(65) Prior Publication Data

US 2005/0004195 A1    Jan. 6, 2005

Related U.S. Application Data

(60) Provisional application No. 60/475,992, filed on Jun. 5, 2003.

(51) Int. Cl.
| | |
|---|---|
| C07D 257/06 | (2006.01) |
| C07D 209/12 | (2006.01) |
| A61K 31/405 | (2006.01) |
| A61K 31/41  | (2006.01) |

(52) U.S. Cl. .................. 514/381; 514/418; 548/251; 548/484

(58) Field of Classification Search ............. 514/381, 514/418; 548/251, 484
See application file for complete search history.

(56) References Cited

U.S. PATENT DOCUMENTS

| | | | |
|---|---|---|---|
| 3,954,748 A |   | 5/1976  | Thominet |
| 4,675,332 A | * | 6/1987  | Connor et al. ............. 514/381 |
| 4,703,053 A |   | 10/1987 | Connor et al. |
| 4,764,525 A |   | 8/1988  | Connor et al. |
| 4,767,776 A |   | 8/1988  | Connor et al. |
| 4,800,211 A |   | 1/1989  | Tischler et al. |
| 4,910,317 A |   | 3/1990  | Connor et al. |
| 4,931,459 A |   | 6/1990  | Connor et al. |
| 5,208,253 A |   | 5/1993  | Boschelli et al. |
| 5,426,113 A |   | 6/1995  | Low |
| 5,468,898 A |   | 11/1995 | Huang et al. |
| 5,565,488 A |   | 10/1996 | Braunlich et al. |
| 5,731,317 A |   | 3/1998  | Lu et al. |
| 6,274,535 B1 |  | 8/2001  | Feurer et al. |
| 6,444,613 B1 |  | 9/2002  | Feurer et al. |
| 6,471,997 B1 |  | 10/2002 | Breton et al. |

FOREIGN PATENT DOCUMENTS

EP    1 227 084 A1    7/2002

OTHER PUBLICATIONS

Boschelli, et al, "Inhibition of E-Selectin-, ICAm-1, and VCAM-1-Mediated Cell Adhesion by Benzo[b]thiophene-, Benzofuran-, Indole-, and Naphthalene-2-carboxamides: Identification of PD 144795 as an Antiinflammatory Agent", J. Med. Chem., 1995, vol. 38, pp. 4597-4614.

David T. Connor, et al, "Novel Benzothiophene-, Benzofuran-, and Naphthalenecarboxamidotetrazoles as Potential Antiallergy Agents", J. Med. Chem., 1992, vol. 35, pp. 958-965.

Pakray, et al, "The Synthesis of Dimethoxyl[1]benzothieno[2,3-c]quinolines", Dep. of Chem, Univ. of S. FL, Sep.-Oct. 1986, pp. 1571-1577.

Oremek, et al, "Synthese von substituierten Benzo [b]thiophenen", Liebigs Ann. Chem., 1980 pp. 1424-1427.

* cited by examiner

*Primary Examiner*—Kamal A. Saeed
*Assistant Examiner*—Susannah L. Chung
(74) *Attorney, Agent, or Firm*—Galina M. Yakovlea; Bryan C. Zielinski

(57) ABSTRACT

The present invention provides indoles of Formula I:

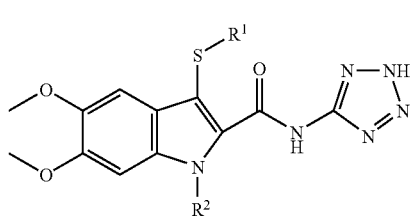

wherein $R^1$ and $R^2$ have any of the values defined therefor in the specification, and pharmaceutically acceptable salts thereof, that are useful as agents in the treatment of diseases and conditions, including inflammatory diseases, cardiovascular diseases, and cancers. Also provided are pharmaceutical compositions comprising one or more compounds of Formula I.

9 Claims, No Drawings

3-SUBSTITUTED INDOLES AND DERIVATIVES THEREOF AS THERAPEUTIC AGENTS

CROSS-REFERENCES TO RELATED APPLICATIONS

This application claims the benefit of U.S. Provisional Patent application Ser. No. 60/475,992 filed on Jun. 5, 2003 the teachings of which are herein incorporated by reference.

BACKGROUND OF THE INVENTION

Phosphoinositide-3-kinases (PI3Ks) are a family of lipid kinases that phosphorylate phosphoinositols on the 3'-OH to generate PI-3-P (phosphatidylinositol 3-phosphate), PI-3,4-P2 and PI-3,4,5-P3. One class of PI3Ks that are stimulated by growth factors include PI3Kα, PI3Kβ, and PI3Kδ. A separate class of PI3Ks are activated by G-protein coupled receptors and include PI3Kγ. The growth-factor stimulated PI3Ks (e.g., PI3Kα), have been implicated in cellular proliferation and cancer. PI3Kγ has been demonstrated to be involved in signaling cascades. For example, PI3Kγ is activated in response to ligands such as C5a, fMLP, ADP, and IL-8. In addition, PI3Kγ has been implicated in immune diseases (Hirsch et al. *Science* 2000;287:1049–1053). PI3Kγ null macrophages show a reduced chemotactic response and a reduced ability to fight inflammation (Hirsch et al., 2000, supra). Furthermore, PI3Kγ has also been implicated in thrombolytic diseases (e.g., thromboembolism, ischemic diseases, heart attacks, and stroke) (Hirsch et al. *FASEB J.* 2000; 15(11):2019–2021; and Hirsch et al. *FASEB J.*, Jul. 9 2001;10.1096/fj.00–0810fje (cited herein as Hirsch et al., 2001).

Inhibitors of members of the PI3Ks are being developed for the treatment of human disease (see e.g., WO 01/81346; WO 01/53266; and WO 01/83456). There is a need for additional compounds that can inhibit PI3Ks for use as pharmaceutical agents.

SUMMARY OF THE INVENTION

In one aspect, the present invention provides for indoles of formula I:

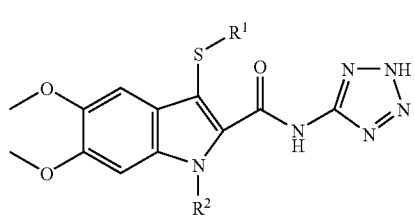

I or a pharmaceutically acceptable salt thereof;
wherein $R^2$ is H or a $C_1$–$C_3$ alkyl; and
wherein $R^1$ is an unsubstituted phenyl or a phenyl substituted with 1, 2, or 3 substituents independently selected from the group consisting of:
$C_1$–$C_4$ alkyl, methyl, $C_1$–$C_4$ alkyl-O, methoxy, halo, Cl, Br, and I. Examples of compounds of Formula II include, but are not limited to:
5,6-Dimethoxy-3-o-tolylsulfanyl-1H-indole-2-carboxylic acid (2H-tetrazol-5-yl)-amide;
3-(3,4-Dichloro-phenylsulfanyl)-5,6-dimethoxy-1H-indole-2-carboxylic acid (2H-tetrazol-5-yl)-amide;
5,6-Dimethoxy-1-methyl-3-phenylsulfanyl-1H-indole-2-carboxylic acid (2H-tetrazol-5-yl)-amide;
5,6-Dimethoxy-3-phenylsulfanyl-1H-indole-2-carboxylic acid (2H-tetrazol-5-yl)-amide;
5,6-Dimethoxy-3-(3-methoxy-phenylsulfanyl)-1H-indole-2-carboxylic acid (2H-tetrazol-5-yl)-amide;
1-Ethyl-5,6-dimethoxy-3-phenyl-1H-indole-2-carboxylic acid (1H-tetrazol-5-yl)-amide; and
5,6-Dimethoxy-3-phenyl-1-propyl-1H-indole-2-carboxylic acid (1H-tetrazol-5-yl)-amide.

In certain embodiments of Formula I, $R^1$ is an unsubstituted phenyl—a compound of Formula II:

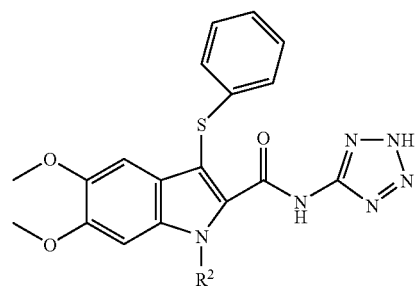

II

Examples of compounds of Formula II include, but are not limited to:
5,6-Dimethoxy-1-methyl-3-phenylsulfanyl-1H-indole-2-carboxylic acid (2H-tetrazol-5-yl)-amide;
5,6-Dimethoxy-3-phenylsulfanyl-1H-indole-2-carboxylic acid (2H-tetrazol-5-yl)-amide;
1-Ethyl-5,6-dimethoxy-3-phenyl-1H-indole-2-carboxylic acid (1H-tetrazol-5-yl)-amide; and
5,6-Dimethoxy-3-phenyl-1-propyl-1H-indole-2-carboxylic acid (1H-tetrazol-5-yl)-amide;

In certain embodiments of Formula I, $R_1$ is a phenyl substituted with 1, 2, or 3 substituents independently selected from the group consisting of: $C_1$–$C_4$ alkyl, methyl, $C_1$–$C_4$ alkyl-O, methoxy, halo, Cl, Br, and I—a compound of Formula III:

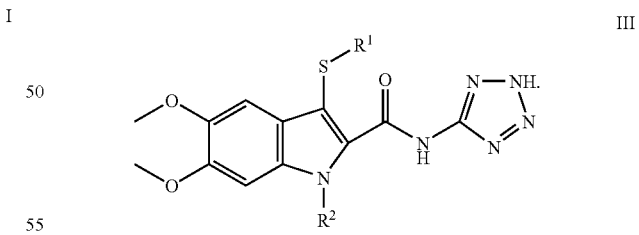

III

Examples of compounds of Formula III include, but are not limited to:
5,6-Dimethoxy-3-o-tolylsulfanyl-1H-indole-2-carboxylic acid (2H-tetrazol-5-yl)-amide;
3-(3,4-Dichloro-phenylsulfanyl)-5,6-dimethoxy-1H-indole-2-carboxylic acid (2H-tetrazol-5-yl)-amide; and
5,6-Dimethoxy-3-(3-methoxy-phenylsulfanyl)-1H-indole-2-carboxylic acid (2H-tetrazol-5-yl)-amide.

In certain embodiments of Formula I, $R_2$ is a $C_1$–$C_3$ alkyl—a compound of Formula IV:

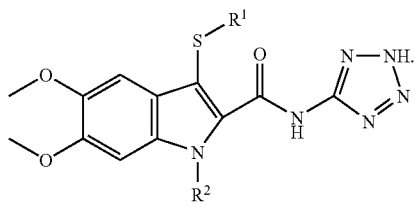

Examples of compounds of Formula IV include, but are not limited to:

5,6-Dimethoxy-1-methyl-3-phenylsulfanyl-1H-indole-2-carboxylic acid (2H-tetrazol-5-yl)-amide;

1-Ethyl-5,6-dimethoxy-3-phenyl-1H-indole-2-carboxylic acid (1H-tetrazol-5-yl)-amide; and 5,6-Dimethoxy-3-phenyl-1-propyl-1H-indole-2-carboxylic acid (1H-tetrazol-5-yl)-amide.

In another aspect, the invention provides for pharmaceutical compositions that comprise a therapeutically effective amount of a compound of Formulas I–IV and a pharmaceutically acceptable carrier. In certain embodiments, these compositions are useful in the treatment of a PI3K-mediated disorder or condition. The compounds of the invention can also be combined in a pharmaceutical composition that also comprise compounds that are useful for the treatment of cancer, a thrombolytic disease, heart disease, stroke, an inflammatory disease such as rheumatoid arthritis, or another PI3K-mediated disorder.

In another aspect, the present invention provides for methods of treating a subject suffering from a PI3K-mediated disorder or condition comprising: administering, to a subject suffering from a PI3K-mediated condition or disorder, a pharmaceutical composition comprising a therapeutically effective amount of a compound of Formulas I–IV and a pharmaceutically acceptable carrier. In certain embodiments, the PI3K-mediated condition or disorder is selected from the group consisting of: rheumatoid arthritis, osteoarthritis, psoriatic arthritis, psoriasis, inflammatory diseases, and autoimmune diseases. In other embodiments, the PI3K-mediated condition or disorder is selected from the group consisting of: cardiovascular diseases, atherosclerosis, hypertension, deep venous thrombosis, stroke, myocardial infarction, unstable angina, thromboembolism, pulmonary embolism, thrombolytic diseases, acute arterial ischemia, peripheral thrombotic occlusions, and coronary artery disease. In still other embodiments, the PI3K-mediated condition or disorder is selected from the group consisting of: cancer, colon cancer, glioblastoma, endometrial carcinoma, hepatocellular cancer, lung cancer, melanoma, renal cell carcinoma, thyroid carcinoma, cell lymphoma, lymphoproliferative disorders, small cell lung cancer, squamous cell lung carcinoma, glioma, breast cancer, prostate cancer, ovarian cancer, cervical cancer, and leukemia. In yet another embodiment, the PI3K-mediated condition or disorder is selected from the group consisting of: type II diabetes. In still other embodiments, the PI3K-mediated condition or disorder is selected from the group consisting of: respiratory diseases, bronchitis, asthma, and chronic obstructive pulmonary disease. In certain embodiments, the subject is a human.

DEFINITIONS

As used herein, the following terms have the meanings ascribed to them unless specified otherwise.

A "PI3K-mediated disorder or condition" is characterized by the participation of one or more PI3Ks or a PI3P phosphatase, (e.g., PTEN, etc.) in the inception, manifestation of one or more symptoms or disease markers, severity, or progression of a disorder or condition. PI3K-mediated disorders and conditions include, but are not limited to: rheumatoid arthritis, osteoarthritis, psoriatic arthritis, psoriasis, inflammatory diseases, pulmonary fibrosis, autoimmune diseases, cardiovascular diseases, atherosclerosis, hypertension, deep venous thrombosis, stroke, myocardial infarction, unstable angina, thromboembolism, pulmonary embolism, thrombolytic diseases, acute arterial ischemia, peripheral thrombotic occlusions, coronary artery disease, cancer, breast cancer, gliobastoma, endometrial carcinoma, hepatocellular carcinoma, colon cancer, lung cancer, melanoma, renal cell carcinoma, thyroid carcinoma, small cell lung cancer, squamous cell lung carcinoma, glioma, prostate cancer, ovarian cancer, cervical cancer, leukemia, cell lymphoma, lymphoproliferative disorders, type II diabetes, respiratory diseases, bronchitis, asthma, and chronic obstructive pulmonary disease.

A PI3K is an enzyme that is able to phosphorylate the 3'-OH of a phosphoinositol to generate PI3P. PI3Ks include, but are not limited to, PI3Kα, PI3Kβ, PI3Kγ, and PI3Kδ. A PI3K typically comprises at least one catalytic subunit (e.g., p110γ), and may further comprise a regulatory subunit (e.g., p101, etc.).

The term "alkyl group" or "alkyl" includes straight and branched carbon chain radicals. The term "alkylene" refers to a diradical of an unsubstituted or substituted alkane. For example, a "$C_{1-4}$ alkyl" is an alkyl group having from 1 to 4 carbon atoms. Examples of straight-chain alkyl groups include, but are not limited to, methyl, ethyl, n-propyl, n-butyl, etc. Examples of branched-chain alkyl groups include, but are not limited to, isopropyl, tert-butyl, isobutyl, etc. Examples of alkylene groups include, but are not limited to, —CH$_2$—, —CH$_2$—CH$_2$—, —CH$_2$—CH(CH$_3$)—CH$_2$—, and —(CH$_2$)$_{1-4}$. Alkylene groups can be substituted with groups as set forth below for alkyl.

Moreover, the term alkyl includes both "unsubstituted alkyls" and "substituted alkyls," the latter of which refers to alkyl moieties having substituents replacing a hydrogen on one or more carbons (e.g., replacing a hydrogen on 1, 2, 3, or 4 carbons) of the hydrocarbon backbone. Such substituents can include, but are not limited to, $C_2$–$C_6$-alkenyl, $C_2$–$C_6$-alkynyl, halo, I, Br, Cl, F, —OH, —COOH, sulfhydryl, ($C_1$–$C_6$-alkyl)S—, $C_1$–$C_6$-alkylsulfinyl, nitro, cyano, trifluoromethyl, —NH$_2$, =O, =S, =N—CN, =N—OH, —OCH$_2$F, —OCHF$_2$, —OCF$_3$, —SCF$_3$, —SO$_2$—NH$_2$, $C_1$–$C_6$-alkoxy, —C(O)O—($C_1$–$C_6$ alkyl), —O—C(O)—($C_1$–$C_6$ alkyl), —C(O)—NH$_2$—C(O)—N (H)—$C_1$–$C_6$ alkyl, —C(O)—N($C_1$–$C_6$ alkyl)$_2$, —OC(O)—NH$_2$, —C(O)—H, —C(O)—($C_1$–$C_6$ alkyl), —C(S)—($C_1$–$C_6$ alkyl), —NR$^{70}$R$^{72}$, where R$^{70}$ and R$^{72}$ are each independently selected from H, $C_1$–$C_6$-alkyl, $C_2$–$C_6$-alkenyl, $C_2$–$C_6$-alkynyl, and C(O)—$C_1$–$C_6$-alkyl.

Typical substituted alkyl groups thus are aminomethyl, 2-nitroethyl, 4-cyanobutyl, 2,3-dichloropentyl, and 3-hydroxy-5-carboxyhexyl, 2-aminoethyl, pentachloroethyl, trifluoromethyl, 2-diethylaminoethyl, 2-dimethylaminopropyl, ethoxycarbonylmethyl, methanylsulfanylmethyl, methoxymethyl, 3-hydroxypentyl, 2-carboxybutyl, 4-chlorobutyl, and pentafluoroethyl.

"Alkoxy" refers to the alkyl groups mentioned above bound through oxygen, examples of which include methoxy, ethoxy, isopropoxy, tert-butoxy, and the like. In addition, alkoxy refers to polyethers such as O—$(CH_2)_2$—O—$CH_3$, and the like. The term "alkoxy" is intended to include both substituted and unsubstituted alkoxy groups. Alkoxy groups can be substituted on carbon atoms with groups such as those set out above for alkyl. Typical substituted alkoxy groups include aminomethoxy, trifluoromethoxy, 2-diethylaminoethoxy, 2-ethoxycarbonylethoxy, 3-hydroxypropoxy, and the like.

"Alkanoyl" groups are alkyl linked through a carbonyl, e.g., $C_1$–$C_6$alkyl—C(O)—. Such groups include formyl, acetyl, propionyl, butyryl, and isobutyryl. The term "alkanoyl" is intended to include both substituted and unsubstituted alkanoyl groups. Alkanoyl groups can be substituted with groups such as those set out above for alkyl.

"Halo" includes fluoro, chloro, bromo, and iodo.

"Alkenyl" means straight and branched hydrocarbon radicals having 2 or more carbon atoms and comprising at least one carbon-carbon double bond and includes ethenyl, 3-buten-1-yl, 2-ethenylbutyl, 3-hexen-1-yl, and the like. The term "alkenyl" is intended to include both substituted and unsubstituted alkenyl groups. A "$C_2$–$C_6$-alkenyl" is an alkenyl group having from from 2 to 6 carbon atoms. Alkenyl groups can be substituted with groups such as those set out above for alkyl. The term "alkenylene" refers to a diradical of a substituted or unsubstituted alkene. Examples of alkenylene groups include, but are not limited to, —CH═CH—, —CH═CH—$CH_2$—, and —$(CH_2)_{1-6}$—CH═CH—$CH_2$—.

"Alkynyl" means straight and branched hydrocarbon radicals having 2 or more carbon atoms and comprising at least one carbon-carbon triple bond and includes ethynyl, 3-butyn-1-yl, propynyl, 2-butyn-1-yl, 3-pentyn-1-yl, and the like. The term "alkynyl" is intended to include both substituted and unsubstituted alkynyl groups. Alkynyl groups can be substituted with groups such as those set out above for alkyl. In certain embodiments, a straight chain or branched chain alkynyl group has 6 or fewer carbon atoms in its backbone (e.g., $C_2$–$C_6$ for straight chain, $C_3$–$C_6$ for branched chain).

The term $C_2$–$C_6$ includes alkynyl groups containing 2 to 6 carbon atoms. The term "alkynylene" refers to a diradical of a substituted or unsubstituted alkyne. Examples of alkynylene groups include, but are not limited to, —CH≡CH—, —C≡C—$CH_2$—, and —$(CH_2)_{1-6}$—C≡C—$CH_2$—.

Some of the compounds in the present invention may exist as stereoisomers, including enantiomers, diastereomers, and geometric isomers. Geometric isomers include compounds of the present invention that have alkenyl groups, which may exist as entgegen or zusammen conformations, in which case all geometric forms thereof, both entgegen and zusammen, cis and trans, and mixtures thereof, are within the scope of the present invention. Some compounds of the present invention have cycloalkyl groups, which may be substituted at more than one carbon atom, in which case all geometric forms thereof, both cis and trans, and mixtures thereof, are within the scope of the present invention. All of these forms, including (R), (S), epimers, diastereomers, cis, trans, syn, anti, (E), (Z), tautomers, and mixtures thereof, are contemplated in the compounds of the present invention.

DETAILED DESCRIPTION OF THE INVENTION

I. Introduction

The present invention relates to indoles of Formulas I–IV, wherein $R^1$, and $R^2$ have any of the values defined therefor in the specification, and pharmaceutically acceptable salts thereof, that are useful as agents in the treatment of diseases and conditions, including inflammatory diseases, cardiovascular diseases, and cancers. Also provided are pharmaceutical compositions comprising one or more compounds of Formulas I–IV.

II. Preparation of Compounds

Compounds of the present invention (e.g., compounds of Formulas I–IV) can be prepared by applying synthetic methodology known in the art and synthetic methodology outlined in the schemes set forth below.

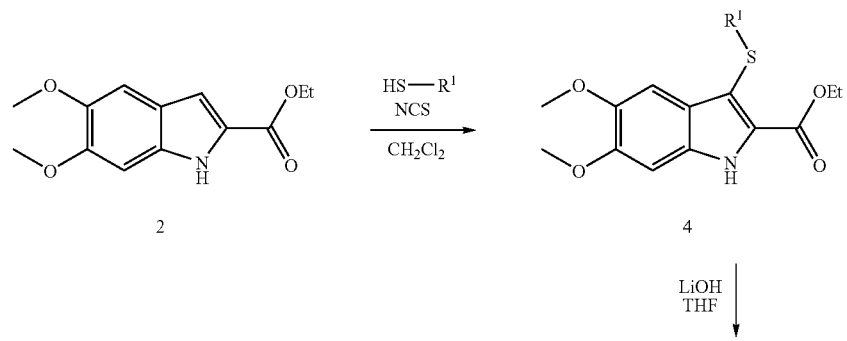

Scheme 1

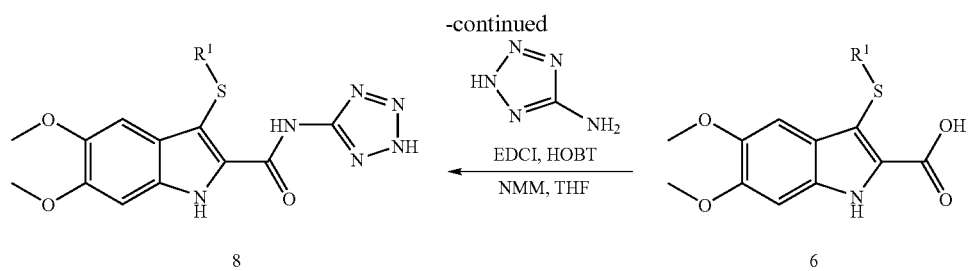

In Scheme 1, compounds of formula I can be synthesized using the depicted synthetic scheme. The 1H-indole-2-carboxylic acid ethyl ester 2 (5,6-dimethoxy-1H-indole-2-carboxylic acid ethyl ester (Lancaster Synthesis Inc., Windham, N.H.)) is reacted in dichloromethane with N-chlorosuccinimide (NCS) treated $R^1$—SH (e.g., 2-methyl benzenethiol, 3,4-dichlorobenzenethiol, benzenethiol, 3-methoxybenzenethiol, etc.) to yield 4 (e.g., 5,6-Dimethoxy-3-o-tolylsulfanyl-1H-indole-2-carboxylic acid ethyl ester). The ester 4 is then saponified with an inorganic base such as LiOH or NaOH in a solution of MeOH and THF; dioxane and water; or methanol and water, to afford the carboxylic acid 6 (e.g., 5,6-Dimethoxy-3-o-tolylsulfanyl-1H-indole-2-carboxylic acid).

The carboxylic acid 6 is then coupled to 5-aminotetrazole by reaction with 4-methylmorpholine (NMM), 1-hydroxybenzotriazole (HOBT) and 1-[3-dimethylamino)propyl]-3-ethylcarbodiimide hydrochloride (EDCI) in a solvent such as tetrahydrofuran to give 8 (e.g., 5,6-Dimethoxy-3-o-tolylsulfanyl-1H-indole-2-carboxylic acid (2H-tetrazol-5-yl)-amide).

(e.g., 5,6-dimethoxy-1-methyl-3-phenylsulfanyl-1H-indole-2-carboxylic acid ethyl ester). 20 is then saponified to the acid 22 as described in Scheme 1. Aminotetrazole is then coupled to 22 as described in Scheme 1 to yield 24.

III. Evaluation of Compounds

Compounds of the present invention (e.g., compounds of Formulas I–IV and pharmaceutically acceptable salts thereof) can be assayed for their ability to inhibit a PI3K. Examples of these assays are set out below and include in vitro and in vivo assays of PI3K activity.

In certain embodiments of the present invention are compounds that selectively inhibit one or more PI3Ks as compared to one or more enzymes including, but not limited to, a cyclic nucleotide dependent protein kinase, PDGF, a tyrosine kinase, a MAP kinase, a MAP kinase kinase, a MEKK, a cyclin-dependent protein kinase. In other embodiments of the invention are compounds that selectively inhibit one PI3K as compared to another PI3K. For example, in certain embodiments, compounds of the present invention

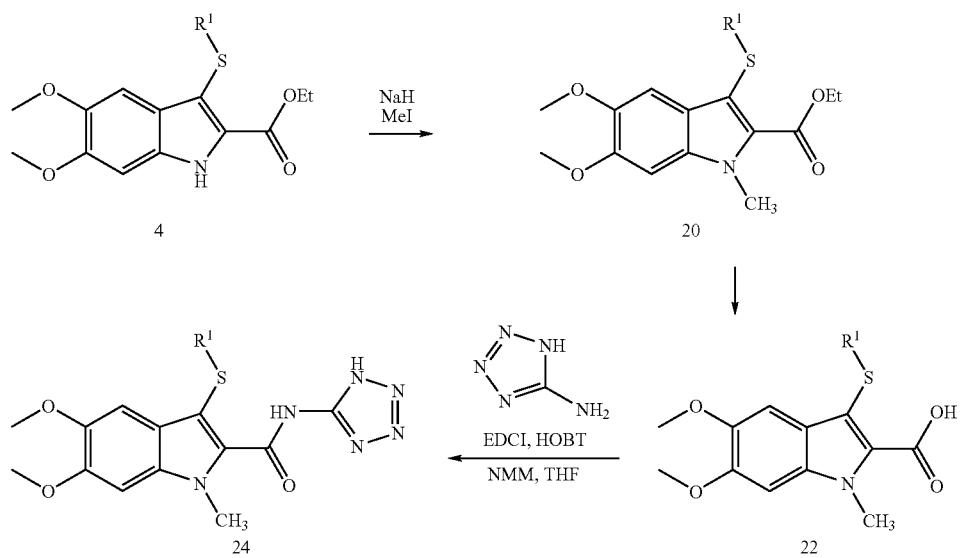

Scheme 2

As shown in Scheme 2, compounds of formula 4 can be alkylated on the indole nitrogen by reaction with a hydride base such as sodium hydride (NaH) and a $C_1$–$C_3$-alkyl halide such as iodomethane in a solvent such as THF and N,N-dimethylformamide to yield the N-alkylated indole 20 display the ability to selectively inhibit PI3Kγ as compared to PI3Kα or PI3Kβ. A compound selectively inhibits a first enzyme as compared to a second enzyme, when the $IC_{50}$ of the compound towards the first enzyme is less than the $IC_{50}$ of the compound towards the second compound. The $IC_{50}$ can be measured, for example, in an in vitro PI3K assay.

In presently preferred embodiments, compounds of the present invention can be assessed for their ability to inhibit PI3K activity in an in vitro or an in vivo assay (see below).

PI3K assays are carried out in the presence or absence of a PI3K inhibitory compound, and the amount of enzyme activity is compared for a determination of inhibitory activity of the PI3K inhibitory compound.

Samples that do not contain a PI3K inhibitory compound are assigned a relative PI3K activity value of 100. Inhibition of PI3K activity is achieved when the PI3K activity in the presence of a PI3K inhibitory compound is less than the control sample (i.e., no inhibitory compound). The $IC_{50}$ of a compound is the concentration of compound that exhibits 50% of the control sample activity. In certain embodiments, compounds of the present invention have an $IC_{50}$ of less than about 100 µM. In other embodiments, compounds of the present invention have an $IC_{50}$ of about 1 µM or less. In still other embodiments, compounds of the present invention have an $IC_{50}$ of about 200 nM or less.

PI3Kγ assays have been described in the art (see e.g., Leopoldt et al. *J. Biol. Chem.*, 1998;273:7024–7029). Typically, a sample containing a complex of p101 and p110γ protein are combined with Gβ and Gγ proteins (e.g., G protein $β_1/γ_2$ subunits). Radiolabeled ATP (e.g., $γ$-$^{32}$P-ATP) is then added to this mixture. The lipid substrates are formed by creating $PIP_2$ containing lipid micelles. The reactions are then started by adding the lipid and enzyme mixtures and are stopped with the addition of $H_3PO_4$. The lipid products are then transferred to a glass fiber filter plate, and washed with $H_3PO_4$ several times. The presence of radioactive lipid product ($PIP_3$) can be measured using radiometric methods that are well-known in the art.

The activity of growth factor regulated PI3Ks can also be measured using a lipid kinase assay. For example, PI3Kα can be assayed using samples that contain a regulatory and a catalytic subunit. An activating peptide (e.g., pY peptide, SynPep Corp.) is added to the sample with radiolabeled ATP. $PIP_2$ containing lipid micelles are then added to the sample to start the reaction. The reactions are worked up and analyzed as described for the PI3Kγ assay just described. Assays can also be carried out using cellular extracts (Susa et al. *J. Biol. Chem.*, 1992;267:22951–22956).

IV. Pharmaceutically Acceptable Salts and Solvates

The compounds to be used in the present invention can exist in unsolvated forms as well as solvated forms, including hydrated forms. In general, the solvated forms, including hydrated forms, are equivalent to unsolvated forms and are intended to be encompassed within the scope of the present invention.

The compounds of the present invention (e.g., compounds of Formulas I–IV) are capable of further forming both pharmaceutically acceptable salts, including but not limited to acid addition and/or base salts. Pharmaceutically acceptable salts of the compounds of formula (I) include the acid addition and base salts (including disalts) thereof. Examples of suitable salts can be found for example in Stahl and Wermuth, *Handbook of Pharmaceutical Salts: Properties, Selection, and Use*, Wiley-VCH, Weinheim, Germany (2002); and Berge et al., "Pharmaceutical Salts," *J. of Pharmaceutical Science*, 1977;66:1–19.

Pharmaceutically acceptable acid addition salts of the compounds of Formulas I–IV include non-toxic salts derived from inorganic acids such as hydrochloric, nitric, phosphoric, sulfuric, hydrobromic, hydriodic, phosphorus, and the like, as well as the salts derived from organic acids, such as aliphatic mono- and dicarboxylic acids, phenyl-substituted alkanoic acids, hydroxy alkanoic acids, alkanedioic acids, aromatic acids, aliphatic and aromatic sulfonic acids, etc. Such salts thus include the acetate, aspartate, benzoate, besylate (benzenesulfonate), bicarbonate/carbonate, bisulfate, caprylate, camsylate (camphor sulfonate), chlorobenzoate, citrate, edisylate (1,2-ethane disulfonate), dihydrogenphosphate, dinitrobenzoate, esylate (ethane sulfonate), fumarate, gluceptate, gluconate, glucuronate, hibenzate, hydrochloride/chloride, hydrobromide/bromide, hydroiodide/iodide, isobutyrate, monohydrogen phosphate, isethionate, D-lactate, L-lactate, malate, maleate, malonate, mandelate, mesylate (methanesulfonate), metaphosphate, methylbenzoate, methylsulfate, 2-napsylate (2-naphthalene sulfonate), nicotinate, nitrate, orotate, oxalate, palmoate, phenylacetate, phosphate, phthalate, propionate, pyrophosphate, pyrosulfate, saccharate, sebacate, stearate, suberate, succinate sulfate, sulfite, D-tartrate, L-tartrate, tosylate (toluene sulfonate), and xinafoate salts, and the like of compounds of Formulas I–IV. Also contemplated are the salts of amino acids such as arginate, gluconate, galacturonate, and the like.

The acid addition salts of the basic compounds are prepared by contacting the free base form with a sufficient amount of the desired acid to produce the salt in the conventional manner. The free base form may be regenerated by contacting the salt form with a base and isolating the free base in the conventional manner. The free base forms differ from their respective salt forms somewhat in certain physical properties such as solubility in polar solvents, but otherwise the salts are equivalent to their respective free base for purposes of the present invention.

Pharmaceutically acceptable base addition salts are formed with metals or amines, such as alkali and alkaline earth metal hydroxides, or of organic amines. Examples of metals used as cations are aluminium, calcium, magnesium, potassium, sodium, and the like. Examples of suitable amines include arginine, choline, chloroprocaine, N,N'-dibenzylethylenediamine, diethylamine, diethanolamine, diolamine, ethylenediamine (ethane-1,2-diamine), glycine, lysine, meglumine, N-methylglucamine, olamine, procaine (benzathine), and tromethamine.

The base addition salts of acidic compounds are prepared by contacting the free acid form with a sufficient amount of the desired base to produce the salt in the conventional manner. The free acid form may be regenerated by contacting the salt form with an acid and isolating the free acid in a conventional manner. The free acid forms differ from their respective salt forms somewhat in certain physical properties such as solubility in polar solvents, but otherwise the salts are equivalent to their respective free acid for purposes of the present invention.

V. Pharmaceutical Compositions and Methods of Administration

This invention also provides for pharmaceutical compositions comprising a therapeutically effective amount of a compound of Formulas I–IV, or a pharmaceutically acceptable salt thereof together with a pharmaceutically acceptable carrier, diluent, or excipient therefor. The phrase "pharmaceutical composition" refers to a composition suitable for administration in medical or veterinary use. The phrase "therapeutically effective amount" means an amount of a compound, or a pharmaceutically acceptable salt thereof, sufficient to inhibit, halt, or allow an improvement in the disorder or condition being treated when administered alone or in conjunction with another pharmaceutical agent or treatment in a particular subject or subject population. For example in a human or other mammal, a therapeutically effective amount can be determined experimentally in a laboratory or clinical setting, or may be the amount required by the guidelines of the United States Food and Drug Administration, or equivalent foreign agency, for the particular disease and subject being treated.

It should be appreciated that determination of proper dosage forms, dosage amounts, and routes of administration is within the level of ordinary skill in the pharmaceutical and medical arts, and is described below.

A compound of the present invention can be formulated as a pharmaceutical composition in the form of a syrup, an elixir, a suspension, a powder, a granule, a tablet, a capsule, a lozenge, a troche, an aqueous solution, a cream, an ointment, a lotion, a gel, an emulsion, etc. Preferably, a compound of the present invention will cause a decrease in symptoms or a disease indicia associated with a PI3K-mediated disorder as measured quantitatively or qualitatively.

For preparing pharmaceutical compositions from the compounds of the present invention, pharmaceutically acceptable carriers can be either solid or liquid. Solid form preparations include powders, tablets, pills, capsules, cachets, suppositories, and dispersible granules. A solid carrier can be one or more substances which may also act as diluents, flavoring agents, binders, preservatives, tablet disintegrating agents, or an encapsulating material.

In powders, the carrier is a finely divided solid which is in a mixture with the finely divided active component. In tablets, the active component is mixed with the carrier having the necessary binding properties in suitable proportions and compacted in the shape and size desired.

The powders and tablets contain from 1% to 95% (w/w) of the active compound. In certain embodiments, the active compound ranges from 5% to 70% (w/w). Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

For preparing suppositories, a low melting wax, such as a mixture of fatty acid glycerides or cocoa butter, is first melted and the active component is dispersed homogeneously therein, as by stirring. The molten homogeneous mixture is then poured into convenient sized molds, allowed to cool, and thereby to solidify.

Liquid form preparations include solutions, suspensions, and emulsions, for example, water or water/propylene glycol solutions. For parenteral injection, liquid preparations can be formulated in solution in aqueous polyethylene glycol solution.

Aqueous solutions suitable for oral use can be prepared by dissolving the active component in water and adding suitable colorants, flavors, stabilizers, and thickening agents as desired. Aqueous suspensions suitable for oral use can be made by dispersing the finely divided active component in water with viscous material, such as natural or synthetic gums, resins, methylcellulose, sodium carboxymethylcellulose, and other well-known suspending agents.

Also included are solid form preparations which are intended to be converted, shortly before use, to liquid form preparations for oral administration. Such liquid forms include solutions, suspensions, and emulsions. These preparations may contain, in addition to the active component, colorants, flavors, stabilizers, buffers, artificial and natural sweeteners, dispersants, thickeners, solubilizing agents, and the like.

The pharmaceutical preparation is preferably in unit dosage form. In such form the preparation is subdivided into unit doses containing appropriate quantities of the active component. The unit dosage form can be a packaged preparation, the package containing discrete quantities of preparation, such as packeted tablets, capsules, and powders in vials or ampules. Also, the unit dosage form can be a capsule, tablet, cachet, or lozenge itself, or it can be the appropriate number of any of these in packaged form.

The quantity of active component in a unit dose preparation may be varied or adjusted from 0.1 mg to 1000 mg, preferably 1.0 mg to 100 mg, or from 1% to 95% (w/w) of a unit dose, according to the particular application and the potency of the active component. The composition can, if desired, also contain other compatible therapeutic agents.

Pharmaceutically acceptable carriers are determined in part by the particular composition being administered, as well as by the particular method used to administer the composition. Accordingly, there is a wide variety of suitable formulations of pharmaceutical compositions of the present invention (see, e.g., *Remington: The Science and Practice of Pharmacy,* 20th ed., Gennaro et al. Eds., Lippincott Williams and Wilkins, 2000).

A compound of the present invention, alone or in combination with other suitable components, can be made into aerosol formulations (i.e., they can be "nebulized") to be administered via inhalation. Aerosol formulations can be placed into pressurized acceptable propellants, such as dichlorodifluoromethane, propane nitrogen, and the like.

Formulations suitable for parenteral administration, such as, for example, by intravenous, intramuscular, intradermal, and subcutaneous routes, include aqueous and non-aqueous, isotonic sterile injection solutions, which can contain antioxidants, buffers, bacteriostats, and solutes that render the formulation isotonic with the blood of the intended recipient, and aqueous and nonaqueous sterile suspensions that can include suspending agents, solubilizers, thickening agents, stabilizers, and preservatives. In the practice of this invention, compositions can be administered, for example, by intravenous infusion, orally, topically, intraperitoneally, intravesically or intrathecally. The formulations of compounds can be presented in unit-dose or multi-dose sealed containers, such as ampules and vials. Injection solutions and suspensions can be prepared from sterile powders, granules, and tablets of the kind previously described.

The dose administered to a subject, in the context of the present invention should be sufficient to affect a beneficial therapeutic response in the subject over time. The term "subject" refers to a member of the class Mammalia. Examples of mammals include, without limitation, humans, primates, chimpanzees, rodents, mice, rats, rabbits, horses, livestock, dogs, cats, sheep, and cows.

The dose will be determined by the efficacy of the particular compound employed and the condition of the subject, as well as the body weight or surface area of the subject to be treated. The size of the dose also will be determined by the existence, nature, and extent of any adverse side-effects that accompany the administration of a particular compound in a particular subject. In determining the effective amount of the compound to be administered in the treatment or prophylaxis of the disorder being treated, the physician can evaluate factors such as the circulating plasma levels of the compound, compound toxicities, and/or the progression of the disease, etc. In general, the dose equivalent of a compound is from about 1 μg/kg to 100 mg/kg for a typical subject. Many different administration methods are known to those of skill in the art.

For administration, compounds of the present invention can be administered at a rate determined by factors that can include, but are not limited to, the $LD_{50}$ of the compound, the pharmacokinetic profile of the compound, contraindicated drugs, and the side-effects of the compound at various concentrations, as applied to the mass and overall health of the subject. Administration can be accomplished via single or divided doses.

Examples of a typical tablet, parenteral, and patch formulation include the following:

TABLET FORMULATION EXAMPLE 1

Tablet Formulation

| Ingredient | Amount |
| --- | --- |
| Compound of Formulas I–IV | 50 mg |
| Lactose | 80 mg |
| Cornstarch (for mix) | 10 mg |
| Cornstarch (for paste) | 8 mg |
| Magnesium Stearate (1%) | 2 mg |
| | 150 mg |

The compounds of the present invention (e.g., a compound of Formulas I–IV, or a pharmaceutically acceptable salt thereof) can be mixed with the lactose and cornstarch (for mix) and blended to uniformity to a powder. The cornstarch (for paste) is suspended in 6 mL of water and heated with stirring to form a paste. The paste is added to the mixed powder, and the mixture is granulated. The wet granules are passed through a No. 8 hard screen and dried at 50° C. The mixture is lubricated with 1% magnesium stearate and compressed into a tablet. The tablets are administered to a patient at the rate of 1 to 4 each day for treatment of a PI3K-mediated disorder or condition.

PARENTERAL SOLUTION FORMULATION EXAMPLE 1

In a solution of 700 mL of propylene glycol and 200 mL of water for injection can be added 20.0 g of a compound of the present invention. The mixture is stirred, and the pH is adjusted to 5.5 with hydrochloric acid. The volume is adjusted to 1000 mL with water for injection. The solution is sterilized, filled into 5.0 mL ampules, each containing 2.0 mL (40 mg of invention compound), and sealed under nitrogen. The solution is administered by injection to a subject suffering from a PI3K-mediated disorder or condition and in need of treatment.

PATCH FORMULATION EXAMPLE 1

Ten milligrams of a compound of the present invention can be mixed with 1 mL of propylene glycol and 2 mg of acrylic-based polymer adhesive containing a resinous cross-linking agent. The mixture is applied to an impermeable backing (30 cm$^2$) and applied to the upper back of a patient for sustained release treatment of a PI3K-mediated disorder or condition.

VI. Methods for Treating PI3K-Mediated Disorders and Conditions

The compounds of the present invention and pharmaceutical compositions comprising a compound of the present invention can be administered to a subject suffering from a PI3K-mediated disorder or condition. PI3K-mediated disorders and conditions can be treated prophylactically, acutely, and chronically using compounds of the present invention, depending on the nature of the disorder or condition. Typically, the host or subject in each of these methods is human, although other mammals can also benefit from the administration of a compound of the present invention.

In therapeutic applications, the compounds of the present invention can be prepared and administered in a wide variety of oral and parenteral dosage forms. The term "administering" refers to the method of contacting a compound with a subject. Thus, the compounds of the present invention can be administered by injection, that is, intravenously, intramuscularly, intracutaneously, subcutaneously, intraduodenally, parentally, or intraperitoneally. Also, the compounds described herein can be administered by inhalation, for example, intranasally. Additionally, the compounds of the present invention can be administered transdermally, topically, via implantation, transdermally, topically, and via implantation. In certain embodiments, the compounds of the present invention are delivered orally. The compounds can also be delivered rectally, bucally, intravaginally, ocularly, andially, or by insufflation.

The compounds utilized in the pharmaceutical method of the invention can be administered at the initial dosage of about 0.001 mg/kg to about 100 mg/kg daily. In certain embodiments, the daily dose range is from about 0.1 mg/kg to about 10 mg/kg. The dosages, however, may be varied depending upon the requirements of the subject, the severity of the condition being treated, and the compound being employed. Determination of the proper dosage for a particular situation is within the skill of the practitioner. Generally, treatment is initiated with smaller dosages, which are less than the optimum dose of the compound. Thereafter, the dosage is increased by small increments until the optimum effect under circumstances is reached. For convenience, the total daily dosage may be divided and administered in portions during the day, if desired. The term "treatment" includes the acute, chronic, or prophylactic diminishment or alleviation of at least one symptom or characteristic associated with or caused by the disorder being treated. For example, treatment can include diminishment of several symptoms of a disorder, inhibition of the pathological progression of a disorder, or complete eradication of a disorder. The compounds of the present invention can be co-administered to a subject. The term "co-administered" means the adminstration of two or more different pharmaceutical agents or treatments (e.g., radiation treatment) that are administered to a subject by combination in the same pharmacetical composition or separate pharamaceutical compositions. Thus co-adminstration involves adminstration at the same time of a single pharmaceutical composition comprising two or more pharmaceutical agents or administration of two or more different compositions to the same subject at the same or different times. For example, a subject that is administered a first dosage that comprises a compound of the present invention at 8 a.m. and then is adminstred CELEBREX® at 1–12 hours later, e.g., 6 p.m., of that same day has been co-administered with a compound of the present invention and CELEBREX®. Alternatively, for example, a subject could be administred with a single dosage comprising a compound of the present invention and CELEBREX® at 8 a.m. has been co-administered with a compound of the present invention and CELEBREX®.

Thus, compounds of the invention can also be co-administered with compounds that are useful for the treatment of cancer (e.g., cytotoxic drugs such as TAXOL®, taxotere, GLEEVEC® (Imatinib Mesylate), adriamycin, daunomycin, cisplatin, etoposide, a vinca alkaloid, vinblastine, vincristine, methotrexate, or adriamycin, daunomycin, cis-platinum, etoposide, and alkaloids, such as vincristine, farnesyl transferase inhibitors, endostatin and angiostatin, VEGF inhibitors, and antimetabolites such as methotrexate. The compounds of the present invention may also be used in combination with a taxane derivative, a platinum coordination complex, a nucleoside analog, an anthracycline, a topoisomerase inhibitor, or an aromatase inhibitor). Radiation treatments can also be co-administered with a compound of the present invention for the treatment of cancers.

The compounds of the invention can also be co-administered with compounds that are useful for the treatment of a thrombolytic disease, heart disease, stroke, etc., (e.g., aspirin, streptokinase, tissue plasminogen activator, urokinase, anticoagulants, antiplatelet drugs (e.g., PLAVIX®); clopidogrel bisulfate), a statin (e.g., LIPITOR® (Atorvastatin calcium), ZOCOR® (Simvastatin), CRESTOR® (Rosuvastatin), etc.), a Beta blocker (e.g, Atenolol), NORVASC® (amlodipine besylate), and an ACE inhibitor (e.g., Accupril® (Quinapril Hydrochloride), Lisinopril, etc.).

The compounds of the invention can also be co-administered for the treatment of hypertension with compounds such as ACE inhibitors, lipid lowering agents such as statins, LIPITOR® (Atorvastatin calcium), calcium channel blockers such as NORVASC® (amlodipine besylate). The compounds of the present invention may also be used in combination with fibrates, beta-blockers, NEPI inhibitors, Angiotensin-2 receptor antagonists and platelet aggregation inhibitors.

For the treatment of inflammatory diseases, including rheumatoid arthritis, the compounds of the invention may be co-administered with agents such as TNF-α inhibitors such as anti-TNFα monoclonal antibodies (such as REMICADE®, CDP-870 and HUMIRA™ (adalimumab) and TNF receptor-immunoglobulin fusion molecules (such as ENBREL®), IL-1 inhibitors, receptor antagonists or soluble IL-1Rα (e.g. KINERET™ or ICE inhibitors), nonsteroidal anti-inflammatory agents (NSAIDS), piroxicam, diclofenac, naproxen, flurbiprofen, fenoprofen, ketoprofen ibuprofen, fenamates, mefenamic acid, indomethacin, sulindac, apazone, pyrazolones, phenylbutazone, aspirin,COX-2 inhibitors (such as CELEBREX® (celecoxib), VIOXX® (rofecoxib), BEXTRA® (valdecoxib) and etoricoxib, metalloprotease inhibitors (preferably MMP-13 selective inhibitors), NEUROTIN®, pregabalin, low dose methotrexate, leflunomide, hydroxychloroquine, d-penicillamine, auranofin or parenteral or oral gold.

The compounds of the invention may be co-administered with existing therapeutic agents for the treatment of osteoarthritis. Suitable agents to be used in combination include standard non-steroidal anti-inflammatory agents (hereinafter NSAID's) such as piroxicam, diclofenac, propionic acids such as naproxen, flurbiprofen, fenoprofen, ketoprofen and ibuprofen, fenamates such as mefenamic acid, indomethacin, sulindac, apazone, pyrazolones such as phenylbutazone, salicylates such as aspirin, COX-2 inhibitors such as celecoxib, valdecoxib, rofecoxib and etoricoxib, analgesics and intraarticular therapies such as corticosteroids and hyaluronic acids such as hyalgan and synvisc.

The compounds of the invention may also be co-administered with antiviral agents such as Viracept, AZT, aciclovir and famciclovir, and antisepsis compounds such as Valant.

The compounds of the present invention may further be co-administered with CNS agents such as antidepressants (such as sertraline), anti-Parkinsonian drugs (such as deprenyl, L-Dopa, Requip, Mirapex, MAOB inhibitors such as selegine and rasagiline, comP inhibitors such as Tasmar, A-2 inhibitors, dopamine reuptake inhibitors, NMDA antagonists, Nicotine agonists, Dopamine agonists and inhibitors of neuronal nitric oxide synthase), and anti-Alzheimer's drugs such as donepezil, tacrine, NEUROTIN®, pregabalin, COX-2 inhibitors, propentofylline or metryfonate.

The compounds of the present invention may additionally be co-administered with osteoporosis agents such as EVISTA® (raloxifene hydrochloride) droloxifene, lasofoxifene or fosomax and immunosuppressant agents such as FK-506 and rapamycin.

EXAMPLES

Examples 1–7

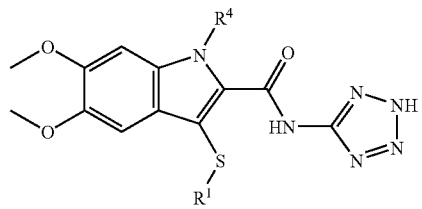

| Ex. | R¹ | R⁴ | MS (M + 1) | ¹H NMR (400 MHz d6-DMSO) |
|---|---|---|---|---|
| 1 | H₃C-(2-methylphenyl) | —H | 411.2 | 16.13 (bs, 1H), 12.27 (s, 1H), 11.63 (s, 1H), 7.21, 7.19 (d, 1H), 7.05–6.96 (m, 3H), 6.72 (s, 1H), 6.64, 6.62 (d, 1H), 3.82 (s, 3H), 3.63 (s, 3H), 2.43 (s, 3H) |

-continued

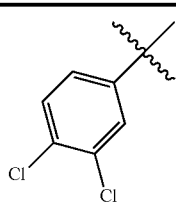

| Ex. | R¹ | R⁴ | MS (M + 1) | ¹H NMR (400 MHz d6-DMSO) |
|---|---|---|---|---|
| 2 | 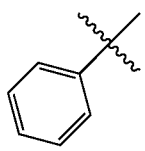 | —H | 465.1 | 16.10 (bs, 1H), 12.33 (bs, 1H), 11.83 (bs, 1H), 7.45 (s, 1H), 7.26 (s, 1H), 7.02, 6.95 (d, 2H), 6.80 (s, 1H), 3.82 (s, 3H), 3.67 (s, 3H) |
| 3 | 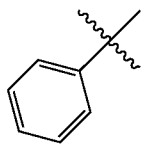 | —CH₃ | 411.2 | 16.13 (bs, 1H), 7.23 (s, 1H), 7.16–7.15 (m, 2H), 7.07–7.05 (m, 1H), 6.98, 6.96 (d, 2H), 6.83 (s, 1H), 3.93 (s, 3H), 3.86 (s, 3H), 3.65 (s, 3H) |
| 4 | 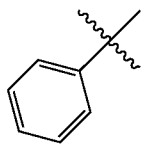 | —H | 397.2 | 16.16 (bs, 1H), 12.27 (s, 1H), 11.64 (s, 1H), 7.22 (t, 2H), 7.13–7.09 (m, 3H), 7.00 (s, 1H), 6.79 (s, 1H), 3.82 (s, 3H), 3.64 (s, 3H) |
| 5 | 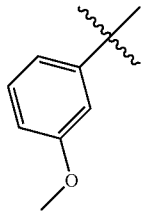 | —H | 427.2 | 16.15 (bs, 1H), 12.29 (s, 1H), 11.63 (s, 1H), 7.15–7.11 (m, 1H), 7.00 (s, 1H), 6.82 (s, 1H), 6.70–6.61 (m, 3H), 3.82 (s, 3H), 3.66 (s, 3H), 3.62 (s, 3H) |
| 6 | 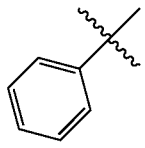 | —CH₂—CH₃ | 425.2 | 16.21 (br-s, 1H), 12.3 (s, 1H), 7.24 (s, 1H), 7.17 (t, 2H), 7.06 (t, 1H), 6.96 (d, 2H), 6.84 (s, 1H), 4.45 (br-q, 2H), 3.87 (s, 3H), 3.66 (s, 3H), 1.33 (t, 3H) |
| 7 | 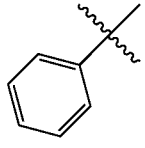 | —(CH₂)₂—CH₃ | 439.2 | 16.12 (br-s, 1H), 12.43 (s, 1H), 7.24 (s, 1H), 7.16 (t, 2H), 7.05 (t, 1H), 6.93 (d, 2H), 6.83 (s, 1H), 4.40 (t, 2H), 3.86 (s, 3H), 3.65 (s, 3H), 1.72 (q, 2H), 0.80 (t, 3H) |

Intermediate 1

5,6-Dimethoxy-3-o-tolylsulfanyl-1H-indole-2-carboxylic acid ethyl ester

To a −78° C. solution of dichloromethane (30 mL) and N-chlorosuccinimide was added 2-methyl benzenethiol (0.709 mL, 6.01 mmol) dropwise. The reaction was allowed to warm 0° C. and then stirred for 30 minutes. 5,6-dimethoxy-1H-indole-2-carboxylic acid ethyl ester (Lancaster Synthesis Inc., Windham, N.H.) (1.5 g, 6.01 mmol) was added drop wise in dichloromethane (15 mL). The reaction was allowed to warm to room temperature and stirred overnight. The reaction was concentrated under reduced pressure. Methanol (5 mL) was added to the residue and a solid formed. The solid was collected, washed with diethyl ether (20 mL) and air dried to yield a beige solid (1.46 g, 66%). MS: M⁺−1=370.2 Da.

Intermediate 2

5,6-Dimethoxy-3-o-tolylsulfanyl-1H-indole-2-carboxylic acid

To a room temperature solution of Intermediate 1 (0.500 g, 1.35 mmol) in methanol (15 mL) and tetrahydrofuran (15 mL) was added 1N lithium hydroxide (2.96 mL, 2.96 mmol). The reaction was stirred overnight and then additional 1N lithium hydroxide (2.96 mL, 2.96 mmol) was added. The reaction was again allowed to stir overnight. The reaction was diluted with ethyl acetate (200 mL) and then acidified to a pH of 2 with 1N hydrochloric acid. The organic layers were washed twice with brine, dried over magnesium sulfate, filtered and concentrated under reduced pressure to yield a crude solid. The solid was collected and washed with 1:1 hexanes/diethyl ether and then air dried to provide the pure product (0.260 g, 56%). MS: $M^+-1=342.1$ Da.

Example 1

5,6-Dimethoxy-3-o-tolylsulfanyl-1H-indole-2-carboxylic acid (2H-tetrazol-5-yl)-amide To a room temperature solution of Intermediate 2 (0.220 g, 0.641 mmol) in tetrahydrofuran (10 mL) was added 4-methylmorpholine (0.14 mL, 1.28 mmol), 1-hydroxybenzotriazole (0.129 g, 0.96 mmol) and 1-[3-dimethylamino)propyl]-3-ethylcarbodiimide hydrochloride (0.183 g, 0.96 mmol) and 5-aminotetrazole (0.054, 0.64 mmol) The reaction was allowed to stir overnight. The reaction was then diluted with ethyl acetate (200 mL). The organic layer was washed twice with 5% citric acid, and then once with brine. The organic layer was dried over magnesium sulfate, filtered and then concentrated in under reduced pressure to yield a crude solid. The solid was collected and washed with diethyl ether to yield the title product (0.128 g, 49%).

Example 2

3-(3,4-Dichloro-phenylsulfanyl)-5,6-dimethoxy-1H-indole-2-carboxylic acid (2H-tetrazol-5-yl)-amide The title compound was synthesized in a manner similar to that described for Example 1 using 3,4-dichlorobenzenethiol instead of 2-methyl benzenethiol. The product was obtained as a yellow powder (0.132 g, 23%).

Intermediate 3

5,6-Dimethoxy-1-methyl-3-phenylsulfanyl-1H-indole-2-carboxylic acid ethyl ester To a 0° C. tetrahydrofuran solution of 5,6-dimethoxy-3-phenylsulfanyl-1H-indole-2-carboxylic acid ethyl ester (0.500 g, 1.40 mmol) was added sodium hydride (95%, 0.037 g, 1.54 mmol) followed by iodomethane (0.096 mL, 1.54 mmol). 5,6-dimethoxy-3-phenylsulfanyl-1H-indole-2-carboxylic acid ethyl ester was synthesized in a manner analogous to Intermediate 1, using benzene thiol instead of 2-methyl benzenethiol. N,N-Dimethylformamide was added to homogenize the reaction. The reaction was allowed to warm to room temperature and stir overnight. The reaction was diluted with ethyl acetate (100 mL). The organic layers were washed with 1N hydrochloric acid (25 mL) and brine (25 mL), dried over magnesium sulfate, filtered and concentrated under reduced pressure to yield the title product, which was used without further purification.

Example 3

5,6-Dimethoxy-1-methyl-3-phenylsulfanyl-1H-indole-2-carboxylic acid (2H-tetrazol-5-yl)-amide The title compound was synthesized in a manner similar to that described for Example 1 using Intermediate 3 instead of Intermediate 1. The product was obtained as a white powder (0.025 g, 11%).

Example 4

5,6-Dimethoxy-3-phenylsulfanyl-1H-indole-2-carboxylic acid (2H-tetrazol-5-yl)-amide The title compound was synthesized in a manner similar to that described for Example 1 using benzenethiol instead of 2-methyl benzenethiol. The product was obtained as a yellow powder (0.079 g, 33%).

Example 5

5,6-Dimethoxy-3-(3-methoxy-phenylsulfanyl)-1H-indole-2-carboxylic acid (2H-tetrazol-5-yl)-amide The title compound was synthesized in a manner similar to that described for Example 1 using 3-methoxybenzenethiol instead of 2-methyl benzenethiol. The product was obtained as a yellow powder (0.024 g, 16%).

Example 6

1-Ethyl-5,6-dimethoxy-3-phenyl-1H-indole-2-carboxylic acid (1H-tetrazol-5-yl)-amide The title compound was synthesized in a manner similar to that described for Example 3 using iodo-ethane instead of iodo-methane as in the synthesis of Intermediate 3.

Example 7

5,6-Dimethoxy-3-phenyl-1-propyl-1H-indole-2-carboxylic acid (1H-tetrazol-5-yl)-amide The title compound was synthesized in a manner similar to that described for Example 3 using 1-iodo-propane instead of iodo-methane as in the synthesis of Intermediate 3.

BIOLOGICAL EXAMPLE 1

PI3Kγ Protein Expression and Purification Protocol

*Spodtera frugiperda* cells, grown in ESF921 media, were coinfected with baculovirus expressing a glu-tagged p101 and baculovirus expressing an HA-tagged p110γ, at a 3:1 ratio of p101 baculovirus to p110γ baculovirus. Sf9 cells were grown to $1\times10^7$ total cells/mL in 10 L bioreactors and harvested 48–72 hours post infection. Samples of infected cells were then tested for expression of p101/p101γ PI3 kinase by immunoprecipitation and Western Blot analysis methods (see below).

To purify PI3Kγ, 4 volumes of room temperature hypotonic lysis buffer (1 mM $MgCl_2$, 1 mM DTT, 5 mM EGTA, 1 mM Pefabloc, 0.5 μM aprotinin, 5 μM leupeptin, 2 μM pepstatin, 5 μM E64, pH 8) per gram of cell paste, was poured onto frozen cell pellets with stirring, then lysed in a nitrogen "bomb" at 400 psi (599HC T316, Parr Instrument Co, Moline, Ill.). NaCl was added to 150 mM, and sodium cholate was added to 1% and mixed for another 45 minutes. The lysates were clarified by centrifugation for 25 minutes at 14,000 rpm. The lysates were then loaded over anti-glu-linked Protein-G Sepaharose beads (Covance Research Products, Richmond, Calif.) using 20 mL resin/50 g cell paste. The column was washed with 15 volumes of wash buffer (1 mM DTT, 0.2 mM EGTA, 1 mM Pefabloc, 0.5 µM aprotinin, 5 µM leupeptin, 2 µM pepstatin, 5 µM E64, 150 mM NaCl, 1% sodium cholate, pH 8). PI3Kγ was eluted with 6 column volumes of wash buffer that contain 100 µg/mL of a peptide that competes for binding of the glu tag. The column fractions with the eluted protein (determined by taking $OD_{280}$ readings) were collected and dialyzed in 0.2 mM EGTA, 1 mM DTT, 1 mM Pefabloc, 5 µM leupeptin, 0.5% sodium cholate, 150 mM NaCl, and 50% glycerol, pH 8. The fractions were stored at −80° C. until further use.

BIOLOGICAL EXAMPLE 2

G Protein Subunits Expression

Spodtera frugiperda cells were coinfected with baculovirus expressing a glu-tagged G protein $β_1$ and baculovirus expressing a G protein $β_2$, at a 1:1 ratio of glu-tagged G protein $β_1$ baculovirus to G protein $β_2$ baculovirus. Sf9 cells are grown in 10 L bioreactors and harvested 48–72 hours post infection. Samples of infected cells were tested for G protein $β_1/β_2$ expression by Western Blot analysis, as described below. Cell lysates were homogenized and loaded onto a column of glu-tagged beads as in Biological Example 1 and competed off the column with a glu peptide and processed as described in Biological Example 1.

BIOLOGICAL EXAMPLE 3

Western Blot Analysis

Protein samples were run on an 8% Tris-Glycine gel and transferred to a 45 µM nitrocellulose membrane. The blots were then blocked with 5% bovine serum albumin (BSA) and 5% ovalbumin in TBST (50 mM Tris, 200 mM NaCl, 0.1% Tween 20, ph 7.4) for 1 hour at room temperature, and incubated overnight at 4° C. with primary antibody diluted 1:1000 in TBST with 0.5% BSA. The primary antibodies for the p110γ, p110α, p110β, p85α, G protein $β_1$, and G protein $γ_2$ subunits were purchased from Santa Cruz Biotechnology, Inc., Santa Cruz, Calif. The p101 subunit antibodies were developed at Research Genetics, Inc., Huntsville, Ala. based on a p101 peptide antigen.

After incubation with the primary antibody, the blots were washed in TBST and incubated for 2 hours at room temperaure with goat-anti-rabbit HRP conjugate (Bio-Rad Laboratories, Inc., Hercules, Calif., product Number 170–6515), diluted 1:10,000 in TBST with 0.5% BSA. The antibodies were detected with ECL™ detection reagents (Amersham Biosciences Corp., Piscataway, N.J.) and quantified on a Kodak ISO400F scanner.

BIOLOGICAL EXAMPLE 4

Immunoprecipitation

100 µL of cell paste from Biological Example 1 or 2 was thawed and lysed on ice with 400 µL of hypotonic lysis buffer (25 mM tris, 1 mM DTT, 1 mM EDTA, 1 mM Pefabloc, 5 µM leupeptin, 5 µM E-64 (Roche), 1% Nonidet P40, pH 7.5–8). The lysate was incubated for 2 hours at room temperature with glu-tagged beads (Covance Research Products, Cambridge, England, product Number AFC-115P). The beads were washed 3 times in wash buffer (20 mM Tris, pH 7.8–8, 150 mM $NaCl_2$, 0.5% NP40) and the protein eluted off the beads by heating in 2 times sample buffer (Invitrogen Corporation, Carlsbad, Calif., product Number LC1676).

BIOLOGICAL EXAMPLE 5

PI3Kγ In Vitro Kinase Assay

The inhibitory properties of the compounds in Table 1 were assayed in an in vitro PI3K assay. In a 96-well polypropylene plate, each well was spotted with 2 µL of 50 times the desired final concentration of compound in DMSO. Purified recombinant p101/p110γ protein (0.03 µg; ~2.7 nM) and G protein $β_1/γ_2$ subunits (0.09 µg; ~57.7 nM) for each reaction was combined in the assay buffer (30 mM HEPES, 100 mM NaCl, 1 mM EGTA, and 1 mM DTT). ATP and [γ-$^{32}$P-ATP] (0.09 µCi) were added to this mixture so that the final ATP concentration in the reaction was 20 µM. Lipid micelles were formed by sonicating phosphatidylinositol-4,5-diphosphate ($PIP_2$), phosphatidylethanolamine (PE), and Na-cholate in the assay buffer for 10 minutes, adding $MgCl_2$ and incubating on ice for 20 minutes, for final concentrations of 25 µM $PIP_2$, 300 µM PE, 0.02% Na-cholate, and 10 mM $MgCl_2$ in the reaction. The reactions were started by adding equal volumes lipid and enzyme mixture in a total volume of 50 µL, allowed to run for 20 minutes at room temperature, and stopped with 100 µL 75 mM $H_3PO_4$. The lipid product was transferred to a glass fiber filter plate and washed with 75 mM $H_3PO_4$ several times. The presence of radioactive lipid product ($PIP_3$) was measured by adding Wallac Optiphase mix to each well and counting in a Wallac 1450 Trilux plate reader (PerkinElmer Life Sciences Inc., Boston, Mass. 02118). The $IC_{50}$ for each compound tested is reported in µM in Table 1:

| Example No. | $IC_{50}$ (µM) |
| --- | --- |
| 1 | 0.585 |
| 2 | 1.845 |
| 3 | 0.550 |
| 4 | 0.210 |
| 5 | 0.725 |
| 6 | 6.6 |
| 7 | 4.145 |

It is understood that the examples and embodiments described herein are for illustrative purposes only and that various modifications or changes in light thereof will be suggested to persons skilled in the art and are to be included within the spirit and purview of this application and the scope of the appended claims. All publications, patents, and patent applications cited herein are hereby incorporated by reference in their entirety for all purposes.

What is claimed is:

1. A compound of Formula I:

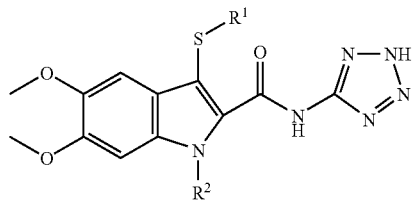

or a pharmaceutically acceptable salt thereof;
wherein $R^2$ is H or a $C_1$–$C_3$ alkyl; and
wherein $R^1$ is an unsubstituted phenyl or a phenyl substituted with 1, 2, or 3 substituents independently selected from the group consisting of:
$C_1$–$C_4$ alkyl, methyl, $C_1$–$C_4$ alkyl-O, methoxy, halo, Cl, Br, and I.

2. The compound of claim 1, wherein wherein $R^1$ is an unsubstituted phenyl.

3. The compound of claim 1, wherein wherein $R^1$ is a phenyl substituted with 1, 2, or 3 substituents independently selected from the group consisting of:
$C_1$–$C_4$ alkyl, methyl, $C_1$–$C_4$ alkyl-O, methoxy, halo, Cl, Br, and I.

4. The compound of claim 1, wherein said compound is selected from the group consisting of:
5,6-Dimethoxy-3-o-tolylsulfanyl-1H-indole-2-carboxylic acid (2H-tetrazol-5-yl)-amide;
3-(3,4-Dichloro-phenylsulfanyl)-5,6-dimethoxy-1H-indole-2-carboxylic acid (2H-tetrazol-5-yl)-amide;
5,6-Dimethoxy-1-methyl-3-phenylsulfanyl-1H-indole-2-carboxylic acid (2H-tetrazol-5-yl)-amide;
5,6-Dimethoxy-3-phenylsulfanyl-1H-indole-2-carboxylic acid (2H-tetrazol-5-yl)-amide;
5,6-Dimethoxy-3-(3-methoxy-phenylsulfanyl)-1H-indole-2-carboxylic acid (2H-tetrazol-5-yl)-amide;
1-Ethyl-5,6-dimethoxy-3-phenyl-1H-indole-2-carboxylic acid (1H-tetrazol-5-yl)-amide; and
5,6-Dimethoxy-3-phenyl-1-propyl-1H-indole-2-carboxylic acid (1H-tetrazol-5-yl)-amide.

5. A method of treating a subject comprising:
administering, to a subject suffering from a disease selected from the group consisting of: rheumatoid arthritis, psoriasis, psoriatic arthritis, osteoarthritis, and a pharmaceutical composition comprising a therapeutically effective amount of a compound of claim 1 and a pharmaceutically acceptable carrier.

6. The method of claim 5, wherein said disease is rheumatoid arthritis.

7. A method of treating a subject comprising:
administering, to a subject suffering from a disease selected from the group consisting of:
asthma a pharmaceutical composition comprising a therapeutically effective amount of a compound of claim 1 and a pharmaceutically acceptable carrier.

8. A pharmaceutical composition comprising:
a therapeutically effective amount of a compound of Formula I:

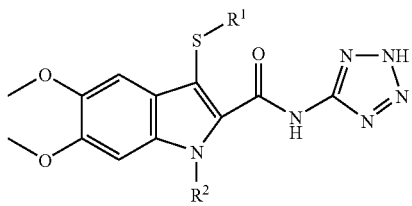

or a pharmaceutically acceptable salt thereof;
wherein $R^2$ is H or a $C_1$–$C_3$ alkyl; and
wherein $R^1$ is an unsubstituted phenyl or a phenyl substituted with 1, 2, or 3 substituents independently selected from the group consisting of:
$C_1$–$C_4$ alkyl, methyl, $C_1$–$C_4$ alkyl-O, methoxy, halo, Cl, Br, and I,
and a pharmaceutically acceptable carrier.

9. A pharmaceutical composition comprising:
a therapeutically effective amount of a compound of any one of claims 2–4 and a pharmaceutically acceptable carrier.

* * * * *